(12) United States Patent
Ricol

(10) Patent No.: US 8,721,522 B2
(45) Date of Patent: May 13, 2014

(54) DUAL BALLOON GASTRIC RING

(75) Inventor: Jean-Paul Ricol, Saint Germain sur l'Arbresle (FR)

(73) Assignee: Compagnie Europeenne d'Etude et de Recherche de Dispositifs l'Implantation par Laparoscopie, Vienne (FR)

( * ) Notice: Subject to any disclaimer, the term of this patent is extended or adjusted under 35 U.S.C. 154(b) by 566 days.

(21) Appl. No.: 12/738,101

(22) PCT Filed: Oct. 16, 2008

(86) PCT No.: PCT/FR2008/001454
§ 371 (c)(1),
(2), (4) Date: Apr. 15, 2010

(87) PCT Pub. No.: WO2009/090334
PCT Pub. Date: Jul. 23, 2009

(65) Prior Publication Data
US 2010/0217071 A1    Aug. 26, 2010

(30) Foreign Application Priority Data
Oct. 16, 2007  (FR) ...................................... 07 07249

(51) Int. Cl.
*A61F 2/00*    (2006.01)
*A61B 17/00*   (2006.01)

(52) U.S. Cl.
USPC .......................................................... 600/37

(58) Field of Classification Search
CPC ............ A61F 5/0003; A61F 2002/045; A61F 2250/0003; A61F 5/0063; A61F 5/0076
USPC ............. 600/29–32, 37; 128/897–899; 604/9; 606/151
See application file for complete search history.

(56) References Cited

U.S. PATENT DOCUMENTS 4,399,809 A * 8/1983 Baro et al. ...................... 600/31

FOREIGN PATENT DOCUMENTS

| EP | 0028962 | 5/1981 |
|----|---------|--------|
| WO | WO2005/009305 | 2/2005 |
| WO | WO2008/022360 | 2/2008 |

\* cited by examiner

*Primary Examiner* — Christine Matthews
*Assistant Examiner* — Joshua D Lannu
(74) *Attorney, Agent, or Firm* — Occhiuti & Rohlicek LLP

(57) ABSTRACT

The invention relates to an implantable surgical ring (1) designed to be closed on itself to form a closed loop (2) having an extension medium axis (XX') for tightening a biological organ (3), wherein said ring (1) includes at least a first and a second ring tightening chamber (12, 13) attached to each other designed to contain a filling fluid for tightening said biological organ (3), said first and second tightening chambers being stepped along the extension medium axis (XX'), said ring being characterized in that the first and second tightening chambers (12, 13) include between them a material-free clearance area (20), in which the wall of the biological organ (3) may move without contacting the ring (1), in order to tighten said biological organ (3) at the level of at least two axially-separated contact areas (14A, 14B).

18 Claims, 2 Drawing Sheets

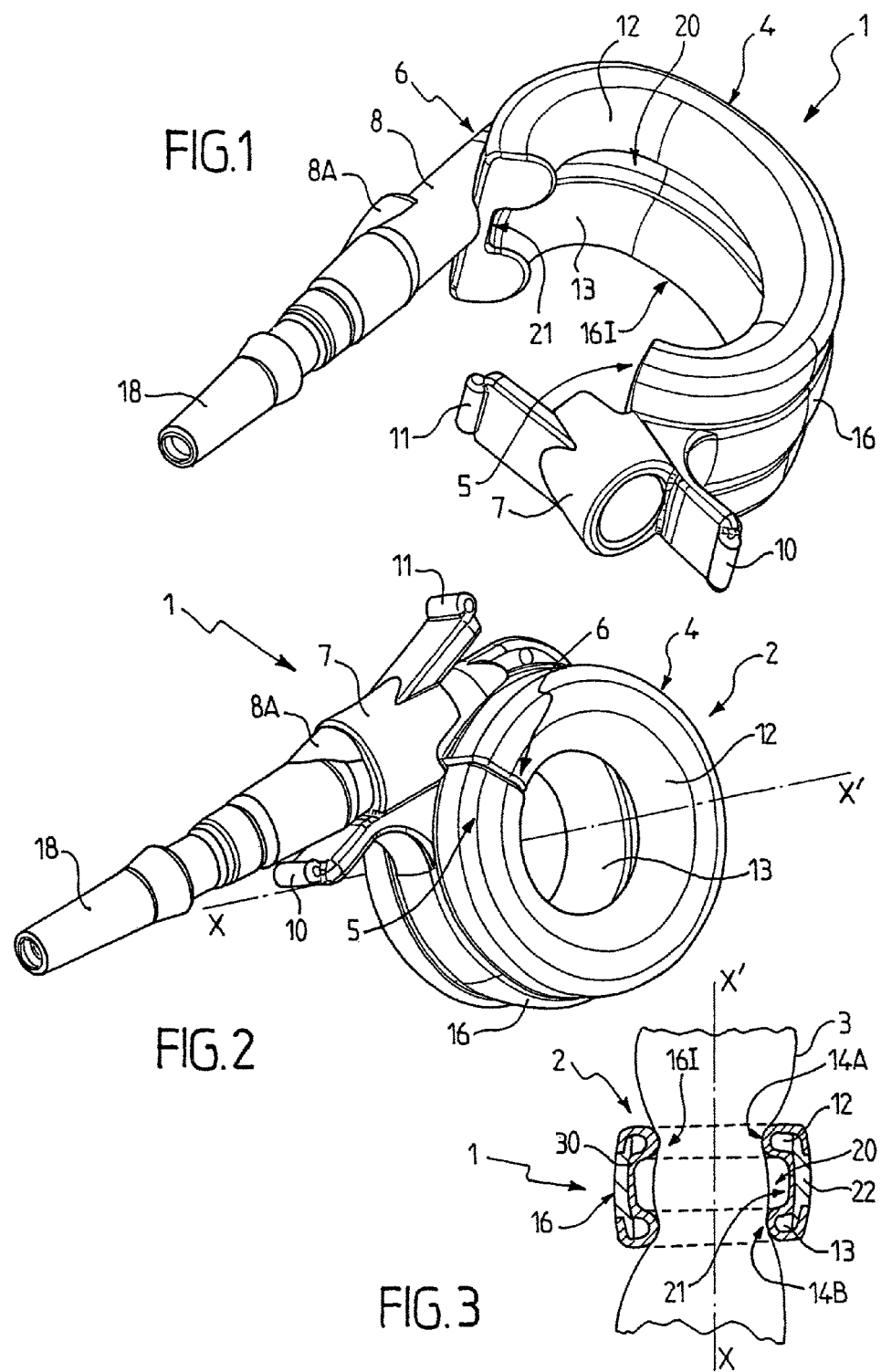

DUAL BALLOON GASTRIC RING

CROSS-REFERENCE TO RELATED APPLICATIONS

This application is the National Stage of International Application No. PCT/FR 2008/001454, filed on Oct 16, 2008, which claims the priority of French Application No. 0707249, filed on Oct 16, 2007. The contents of both applications are hereby incorporated by reference in their entirety.

TECHNICAL DOMAIN

The present invention relates to the general technical domain of surgical implants designed to be implanted in the body of a patient, around (a) biological organ(s) forming a pouch or a duct, and more specifically, gastric rings forming a closed loop around the stomach in order to reduce the diameter of the opening of the stoma.

More specifically, the present invention involves an implantable surgical ring to be closed on itself to form a closed loop having an extension medium axis (XX') for tightening a biological organ forming a pouch or duct in order to modify the diameter of the opening into said organ.

The present invention also involves a method to manufacture such an implantable surgical ring.

PRIOR TECHNIQUE

Surgical intervention is already known in patients suffering from severe obesity who, due to their excess weight, are not only exposed to physical discomfort, but also to psychological problems as well as related disorders, such as diabetes, cardiovascular disease and even severe arthritis.

In particular, a known technique consists of creating a gastric restriction reducing the size of the stomach and, as a result, the intake of food.

For this purpose, gastroplasty rings are often used. They are implanted around the stomach of the patient in order to reduce its volume as well as the diameter of its opening (stoma).

It is well known that such gastroplasty rings in general consist of a flexible band, made of an elastomer, designed to be closed towards these two extremities by means of an appropriate closure system, in order to enclose the stomach.

Moreover, the known rings in general feature an annular tightening chamber located on the inner side of the flexible band whose volume can be adjusted by the addition or withdrawal of a fluid. Therefore, it is possible, with a fixed established diameter of the ring, to however slightly regulate the inner diameter of said ring by the radial expansion or contraction of the chamber.

Such implantable rings are in general satisfactory although they involve a certain number of drawbacks, in particular due to certain uncontrolled changes in their position during the period of treatment.

In fact, the rings in the prior art are sometimes subject to shifts provoked by the natural movements of dilation and contraction of the stomach.

In certain cases, these movements may even lead to the expulsion of the ring by sliding or even by turning over, so that it becomes therapeutically non-operational and results in discomfort for the patient.

In such a situation, it is thereby necessary to carry out another surgical intervention in order to replace or reposition the accidentally displaced ring.

Of course, such corrective surgical operations needlessly mobilise the medical personnel, causes additional disagreement for the patient or even exposes the latter to post-surgical complications.

DESCRIPTION OF THE INVENTION

The present invention consequently seeks to rectify the various drawbacks listed above, and to propose a new implantable surgical ring, specifically a gastric ring, which offers improved stability guaranteeing lasting retention in functional position after implant.

Another object of the present invention features a new implantable surgical ring that is non-traumatic and is especially respectful of the surrounding tissue.

Another object of the invention features a new surgical ring that presents a simple and light structure.

Another object of the present invention features a new surgical ring that is easy and inexpensive to produce.

Another object of the invention features a new method to manufacture an implantable surgical ring that provides said ring with excellent stability once implanted.

Finally, another object of the invention features a new method for the manufacture of a surgical ring that is simple, inexpensive and fast.

The designated objects of the invention are achieved with the help of an implantable surgical ring designed to be closed on itself to form a closed loop having an extension medium axis (XX') for tightening a biological organ forming a pouch or a duct in order to modify the cross section of flow into said organ, said ring comprising at least a first ring tightening chamber and a second ring tightening chamber attached to each other and designed to contain a filling fluid for tightening said biological organ by said ring, said first and second tightening chambers being stepped or offset along the extension medium axis (XX') of the loop, said ring being characterised in that the first and second tightening chambers include between them a material-free clearing area, in which the wall of the biological organ may move without coming into contact with the ring, in order to tighten said biological organ at the level of at least two axially-separated contact areas.

The designated objects of the invention are also achieved with a method for the manufacture of an implantable surgical ring designed to be closed on itself to form a closed loop having an extension medium axis (XX') in order to tighten a biological organ forming a pouch or a duct in order to modify the cross section of flow into said organ, said method comprising a preparation step (a) during which at least a first ring tightening chamber and a second ring tightening chamber are each designed to contain a filling fluid, a step (b) involving stepping in which said first and second tightening chambers are mechanically attached to each other by stepping along the extension medium axis (XX') of the loop (2), said method characterised in that the step (b) involving stepping includes a sub-step (b2) involving delimitation during which a material-free clearance area is provided between the first and second tightening chambers in which the wall of the biological organ may move without coming into contact with the ring so that the first and second tightening chambers are able to tighten the biological organ at the level of at least to axially-separated contact areas.

BRIEF DESCRIPTION OF THE DRAWINGS

Other objects, characteristics and advantages of the invention will become more apparent upon reading the following description, as well as with the help of the attached drawings, which are solely for illustration and not limiting, in which:

FIG. 1 shows, in a perspective view, a surgical ring in compliance with the invention, shown open.

FIG. 2 shows, in a perspective view, the surgical ring in FIG. 1, shown closed.

FIG. 3 shows, in longitudinal section view diagram, a surgical ring in compliance with the invention, shown closed around a biological organ in order to tighten the latter.

BEST WAY TO CARRY OUT THE INVENTION

In the following description, reference will be made, solely as an example and by convenience of description, to a gastroplasty ring (or gastric or stomach ring) designed to encircle the stomach in order to reduce the diameter of the opening of the stoma, or designed to be implanted around the oesophagus.

However, the invention is in no way limited to this application, and also in general covers other surgical rings designed to be implanted in the body of a patient around a biological organ forming a pouch or a duct in order to modify the cross section of flow into said organ when it is constricted by the ring.

Therefore, the invention may be used to treat urinary or faecal incontinence, or even to regulate the blood flow.

According to the application, the surgical ring will of course be adapted to the dimensions, environment, and sensitivity of the organ concerned by the constriction, such as bladder, urethra, intestine, artery, vein, etc.

The implantable surgical ring 1 in the invention is designed to be closed on itself for forming a closed loop 2 having an extension medium axis (XX') in order to tighten a biological organ 3, such as the stomach, forming a pouch or a duct in order to modify the cross section of flow into said organ, as shown in FIG. 3.

Figure 5:
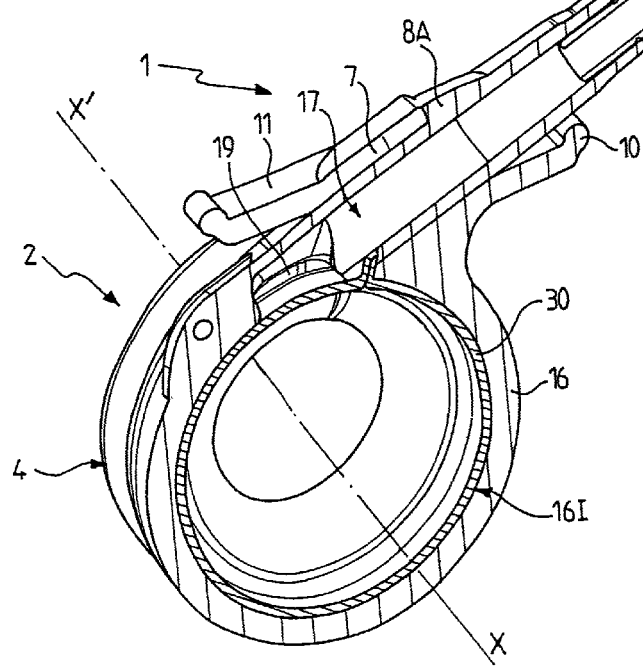
FIG. 5 shows, in a sagittal section view, the variant of a surgical ring in compliance with that represented in FIGS. 1, 2 and 4.

More specifically, said surgical ring 1 has at least an elongated flexible portion 4, preferably made of an elastomer such as silicon, and designed to change from an open configuration, shown in FIG. 1 to a closed configuration, in particular shown in FIGS. 2 and 5, wherein said flexible portion is approximately closed towards its two extremities 5, 6 by means of an appropriate closure system 7, 8, in order to form aforementioned closed loop 2.

Thereby, by enclosing the organ 3 inside the loop 2, it is possible to reduce the diameter of its cross section of flow and, in the specific case of the stomach, the opening of the stoma.

The means of closing 7, 8 is designed to cooperate in order to allow for the locking of ring 1 in its closed configuration. By way of example, for this purpose a collar 7 may be used that is mounted on the first extremity 5 of the flexible portion 4 and designed to receive a rod 8 associated with the second extremity 6, said rod 8 preferably comprising one or several snugs 8A in order to allow for the latching with the collar 7, Of course, the shape adopted by the closed loop 2 is in no way restricted but preferably presents an approximately round contour, and preferentially a circular contour.

Therefore, the extension medium axis (XX') in the invention corresponds to the generating line of the cylindrical collar that forms the surgical ring 1 when it is in closed configuration. According to one preferential variant, surgical ring 1 approximately forms, in closed position, a cylinder with a circular base and the extension medium axis (XX') corresponds to the straight line forming the axis of rotation of said ring.

In addition, the ring 1 may be equipped with one or several holding tabs 10, 11 designed to facilitate its handling by coelioscopy, in particular when it is opened and/or closed.

According to an important characteristic of the invention, surgical ring 1 comprises at least a first ring tightening chamber 12 and a second ring tightening chamber 13 stepped along the extension medium axis (XX') of loop 2 in order to tighten the organ 3 by ring 1 at the level of at least two axially-separated contact areas 14A, 14B.

Therefore, said first and second tightening chambers 12, 13 advantageously provide a double fixation for ring 1 on organ 3, thereby improving the stability of said ring even if said ring temporarily loses its hold on a first point of fixation, a second point of fixation still remains to retain it.

In other terms, the means of fixation in the invention multiply the points of retention of the ring 1 on the organ 3, and thereby considerably reduce the kinetic conditions that a shift of said ring with respect to said organ are united at the same time.

As a result, the possibility of the shift or even release of the ring is considerably limited.

In order to provide a hold that is stable, non-traumatic, and preferably adjustable, the first and second tightening chambers 12, 13 are designed to contain a filling fluid, such as a saline solution or even a gas such as air.

Although said first and/or second tightening chambers 12, 13 may, according to a non represented variant, be sealed so as to contain a fixed volume of filling fluid predetermined by construction, said first and second tightening chambers 12, 13 are preferably connected to an admission and control device, for example comprising an implantable site placed under the patient's skin to allow for the transfer of fluid to or from said chambers by pricking said site with a hollow needle.

In addition, the volume of the first and/or second tightening chamber 12, 13 may be adjusted, that is, delimited by an elastic membrane likely to become deformed according to the pressure of the filling fluid found in the tightening chamber, so that the expansion or contraction of said chamber may be controlled by adding or withdrawing filling fluid.

In particular, the first and second tightening chamber may advantageously be designed so as to enable the fine control of the opening of the stoma as a function of their centripetal radial expansion or, on the contrary, their centrifugal radial contraction.

Of course, the control of the filling fluid in the first and second tightening chamber 12, 13 is adapted to the aforementioned double fixation.

Therefore, according to a preferential characteristic of the invention, the first and second tightening chambers 12, 13 are either in free 2-way fluidic communication, or approximately void of the means of fluidic communication between them.

« Free 2-way fluidic communication », , indicates that the first and second tightening chambers 12, 13 communicate with each other by means of one or several significant sized openings and do not create an obstacle to the circulation of filling fluid, so that said filling fluid may freely move from the first to the second chamber, and conversely, freely move from the second to the first chamber.

According to such an arrangement, the free communication between the tightening chambers enables rapid or even almost-instantaneous transfer of filling fluid and, as a result, the rapid or even instantaneous balancing of the pressure inside said chambers along with the natural movements of the stomach wall.

More specifically, although the temporary fluctuations in the pressure exerted by the stomach membrane on one of the tightening chambers 12, 13 may lead to the partial flow of fluid contained in one of the tightening chambers towards the other tightening chamber, and a global increase in the inner pressure within said chambers 12,13, the relaxing of the stress exerted by the stomach membrane is quickly or even immediately followed by a return to the equilibrium of the system, so that the actual effort of tightening the stomach wall by surgical ring 1 is roughly maintained at the level at each of the contact areas 14A, 14B.

Although the fluidic communication between the chambers may be established by an accessory external circuit, possibly off-set to the level of a joint admission system presenting an adequate flow, the means of free 2-way fluidic communication are preferably located at the level of ring 1 itself and integrated within the latter.

Advantageously, ring 1 may thereby be equipped with a joint admission collector 17 that ensures the fluidic communication between the first and second tightening chamber 12, 13 on the one hand and, the communication between said tightening chambers 12, 13 on the other hand, and a device for the transfer of external fluid to the ring, such as a catheter (not represented), for example by means of an appropriate connexion piece 18.

According to one variant not represented, the joint admission collector may be off-set and include a joint catheter forming a single main duct, with which communicate a plurality of secondary catheters each opening into a tightening chamber 12, 13. In particular, if the ring has two chambers, the collector may also come in the form of a Y-shaped fitting.

Figure 4:
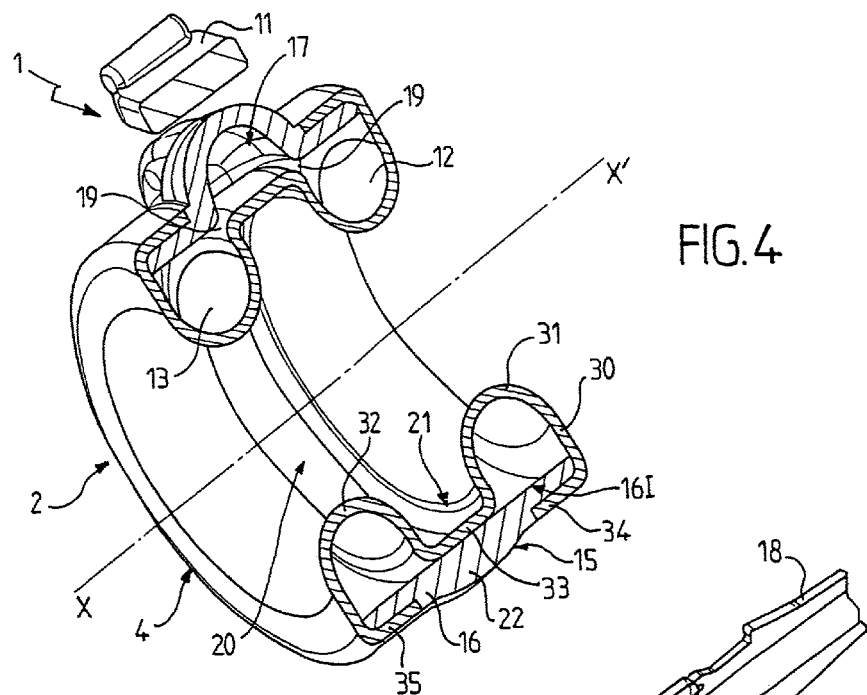
FIG. 4 shows, in a perspective view with partial evulsion, the variant of an implantable ring corresponding to FIGS. 1 and 2.

According to another variant shown in FIGS. 4 and 5, the joint admission collector 17 may be integrated or coupled with the ring. In particular, said collector 17 may be formed by an external radial swelling that tangentially approaches the dorsal portion of ring 1, roughly at the level of the sagittal plane of said ring, and that opens in an approximately symmetrical manner onto each of the first and second tightening chambers 12, 13 by means of inlets 19 specially designed for this purpose.

Such a simple and compact arrangement enables the roughly equal and rapid distribution of the filling fluid within said first and second tightening chambers, in particular at the time of the initial inflation of the latter.

Moreover, according to a variant (not represented), the first and second tightening chambers 12, 13 may be approximately void of the means of fluidic communication between them, that is, be roughly isolated from each other so that no significant transfer of fluid is possible from the first towards the second tightening chamber, and conversely, from the second towards the first tightening chamber, within the normal operation of the device.

In particular, said first and second tightening chambers 12, 13 may then be totally isolated from each other, in an impenetrable manner, without the possibility of exchanging filling fluid, directly or indirectly through their respective admission systems (catheter, implantable site, pump, etc.), the latter being fitted and separated as a consequence.

Nevertheless, it is not excluded, according to the invention, that the organ(s) of separation that may be designed between said first and second tightening chambers 12, 13 present a certain porosity, so that a slight transfer of fluid with a very low flow, in particular an oozing, may nevertheless occur between said chambers, in particular when there is lasting excess pressure inside one of said chambers.

However, although such functioning by « damped » transfer may be considered as part of the invention, it will preferably be roughly symmetrical, that is, will approximately equally affect the transfer of fluid from the first chamber towards the second chamber and the transfer from the second chamber towards the first.

More generally, whatever the type of system of communication or isolation chosen, the latter will preferably be approximately balanced, that is, will not tend to favour the transfer of filling fluid from the first chamber towards the second, or from the second chamber towards the first, that is, the transfer of fluid towards one of the chambers to the detriment of the other chamber.

In particular, said system of communication or isolation may advantageously be dimensioned so as not to cause a lasting imbalance due to the retention of fluid in one of tightening chambers 12, 13 accompanied by a lasting fluid depletion in the other chamber. In other terms, the system of fluid control used within ring 1 in the invention will preferably not provoke the lasting slackening of the tightening stress exerted by either one of the chambers, that is, will not lastingly deprive the ring of either one of its points of bearing, and will allow for an approximately simultaneous and permanent maintenance of the bearing stress in both corresponding areas of contact 14A, 14B.

Moreover, according to another characteristic of the invention, the first and second tightening chambers 12, 13 are advantageously attached to each other.

Therefore, said first and second tightening chambers 12, 13 are kinetically bound, and more specifically are integral at least according to the extension medium axis (XX'), so that each tightening chamber is able to retain the other when the latter tends to slide or roll along the stomach wall. In other terms, the redundancy of the tightening chambers provides for the mutual retention of said chambers and thereby secures the overall retention of the ring 1.

For this purpose, said first and second tightening chambers 12, 13 may be attached to each other by any appropriate means of connexion 15, in particular by cables, rods, strips, plaiting, etc.

Nevertheless, in a preferential manner, the surgical ring 1 comprises a flexible band 16 whose length roughly corresponds to the perimeter of loop 2, the first and the second tightening chamber 12, 13 being fixed to said flexible band 16 so as to make the latter protrude on the inner side 161.

Preferably tightening chambers 12, 13 roughly extend over the entire length of said flexible band 16, and particularly preferentially in a continuous manner. Of course, it is also possible that the « ring » tightening chambers 12, 13 only cover a portion of said flexible band, that is, one and/or the other are divided lengthwise by more or less extensive areas of interruption and/or present an angular cover inferior to 360° around the extension medium axis (XX').

Advantageously, the means of connexion 15, and in particular the flexible band 16, may form the dorsal wall of the ring 1, and in particular delimit the first and second tightening chambers 12, 13 roughly opposite their areas of contact 14A, 14B respective with the organ to encircle 3, as shown in the figures.

According to one variant of the invention, the flexible band 16 may also present a certain memory of shape so that it spontaneously adopts, when at rest, a curved shape tending to « prepare » loop 2, as shown in FIG. 1.

Of course, said flexible band is sufficiently flexible to bend, in order to give loop 2 its curve around the extension axis (XX').

However, according to a preferential variant of the invention, it will present a certain resistance to extension in traction, in parallel to the extension medium axis (XX'), so as to roughly prevent the first tightening chamber 12 from moving away from the second tightening chamber 13 according to this direction, and vice-versa.

According to an alternative variant (not represented), said flexible band 16, and more globally the means of connexion 15, may on the contrary be equipped with means of axial adaptation designed to allow for a certain relative axial clearance of the tightening chambers 12, 13 within limits predefined by construction.

Such a constructive arrangement advantageously lets the ring adopt an especially flexible behaviour enabling it to roughly accompany the movements, in particular peristaltic movements, of the stomach according to their axial component. This lets the ring maintain a good footing without creating the sensation of discomfort for the patient, or provoking the abrasion of the stomach wall.

For this purpose, the means of axial adaptation may, for example, be fitted with elastic articulation organs able to deform in order to « absorb » an axial extension (under traction) or contraction (under compression) of ring 1, or even comprise preferential areas of deformation made supple by the removal of material, such as nicks or slots arranged in the flexible band 16.

Moreover, according to a preferential variant, surgical ring 1 presents, between the first tightening chamber 12 and the second tightening chamber 13, a material-free clearance area 20.

Advantageously, such a constructive arrangement roughly limits the actual contact between the organ 3 and the ring 1 only at the areas of contact 14A, 14B that correspond to the crests of the tightening chambers 12, 13 protruding on the inner side of the ring 1.

In addition, this constructive arrangement has several functional advantages.

On the one hand, it makes ring 1 approximately non-traumatic, since it limits the extent of contact between the organ 3 and the ring 1 only to the useful functional surfaces 14A, 14B of the latter and, as a result, considerably reduces the risk of necrosis or irritation of the stomach wall.

In particular, the stomach wall may also evolve relatively freely in the clearance area 20, and in particular present a bulge between the first and second tightening chamber without coming into contact with any portion of the ring, thereby avoiding bruising said stomach wall.

In addition, the clearance area 20 helps delimit a transition between the first tightening chamber 12 and the second tightening chamber 13, which forms a border of mechanical isolation due to the discontinuity of the contact between the stomach membrane and the ring at the level of said clearance area 20.

This spatial discontinuity between the two contact areas 14A, 14B advantageously renders the ring independent in each of these contact areas 14A, 14B, and more specifically avoids that a slip of said ring 1 by rupture of the contact in the first contact area 14A induces the global slip of the ring, by continuous prolongation of the conditions for the appearance of such a dynamic phenomenon, at the level of the second contact area 14B.

Preferably, the clearance area 20 roughly extends over the entire perimeter of loop 2, so that, once ring 1 is implanted, respective contact areas 14A, 14B between the organ 3 and the first and second tightening chambers 12, 13 are separate.

Therefore, by completely separating contact areas 14A, 14B, ring 1 in the invention presents two lines, or more exactly two distinct, separate and preferably relatively narrow contact bands 14A, 14B, on which the pressure is distributed.

The ring in the invention thereby differs from rings from prior art that, whatever the thickness of their tightening chamber (measured according to the extension medium axis (XX')), they present a single contact band creating a continuous and localised hold on the organ 3 and, as a result, are subject to slipping or turning over as soon as the contact is broken at the level of this single contact band, even if it is relatively wide.

On the contrary, within ring 1 in the invention, the clearance area avoids the continuity between the contact areas 14A, 14B, thereby limiting the propagation of slide phenomena of ring 1 with respect to the stomach wall.

Thereby, this considerably reduces the risk of inversion of the ring by rotation around the medium line that follows the perimeter of loop 2.

In fact, even supposing that the stomach wall would tend to « shift » outside of ring 1 according to the direction (XX') and, as a result, tend to make the first tightening chamber 12 flip over by drawing the latter by friction according to a peeling effect, it is easy to understand that the break in contact induced by the clearance area 20 between the stomach wall and the ring inner wall prevents the continuous propagation of this peeling effect.

On the contrary, as soon as the means of connexion 15 presents a certain rigidity with respect to a flexion around an axis included in a normal plane to the extension medium axis (XX') and roughly tangent to the dorsal of the ring, the « internal peeling » of the first tightening chamber 12 may favour the appearance of a lever phenomenon of the hanging type by which the second tightening chamber 13 tends to reinforce its bearing on organ 3.

Preferably, the clearance area 20 comprises a hollow 21 created on the inner side 161 of the flexible band 16 the bottom of which is placed behind the first and second tightening chambers 12, 13, thereby advantageously allowing the ring to remain at a distance from the wall of the organ 3 in said clearance area 20, or even roughly beyond the range of said organ 3, when said ring is implanted, and the tightening chambers are inflated.

Therefore, as shown in particular in FIGS. 3 and 4, the clearance area 20 may appear in the form of a trench or a recessed notch between said first and second tightening chambers 12, 13, the bottom of said trench or notch located at a greater distance from the extension medium axis (XX') than the crests of said tightening chambers 12, 13 forming the contact areas 14A, 14B with the organ 3.

Advantageously, hollow 21 is sufficiently extended, and in particular sufficiently deep, that is, the disconnection is sufficiently marked, to avoid the continuity between said contact areas 14A, 14B, the recess thereby created allows for this discontinuity to roughly remain on a permanent basis, whatever the behaviour of the organ 3 and the action of the latter on the ring 1.

Moreover, ring 1 in the invention preferably comprises an anti-proximity element 22 placed between the first and second tightening chamber 12, 13 and designed in order to maintain a predetermined minimum separation between the latter.

More specifically, this anti-proximity element 22 helps preserve a minimum width of the recess 21, that is, keep the first and the second tightening chamber 12, 13 away from each other by opposing, at least in part, the settling of the ring by compression according to the extension medium axis (XX').

Advantageously, this thereby avoids any appearance, even accidental, of continuity between the contact areas 14A, 14B.

The anti-proximity element 22 may in particular be formed by a semi-rigid brace or any equivalent means. Preferably, said anti-proximity element 22 is formed by a reinforced portion of the flexible band 16, for example, excess dorsal thickness and/or ribbing.

It is moreover remarkable that, although the means of connexion 15, and more specifically the flexible band 16, may, according to one variant of the invention, allow for the maintenance of an approximately set axial distance between the first and second tightening chambers 12, 13, by both opposing their distance and their proximity according to this axis, said means of connexion 15 may advantageously present a certain radial flexibility, so as to enable a certain relative clearance of said first and second tightening chambers 12, 13 according to directions intersecting the axis of extension (XX').

Thereby, by avoiding the rigid constriction of the stomach of said patient over a relatively long section, the ring in the invention does not create any significant discomfort for said patient.

Of course, the anti-proximity element 22 may indifferently be adapted to maintain a set axial distance between the tightening chambers 12, 13, or even to set a minimum threshold of residual distance in case the means of connexion authorises a certain proximity of said tightening chambers.

According to one preferential variant of the invention, the first and second tightening chambers 12, 13 are delimited by a joint membrane 30 designed to be in contact with the organ 3 to encircle.

In other terms, the inner walls of said first and second tightening chambers 12, 13 designed to come into contact with the organ 3 are advantageously formed integrally.

Preferably, said joint membrane 30 is made of an elastomer, has a roughly constant thickness, preferably less than that of the flexible band 16 forming the dorsal side of the ring 1.

Preferably, the joint membrane 30 is also coupled, at least along part of its length, with the inner side 161 of the flexible band 16 to form the clearance area 20.

In other terms, the first and second tightening chambers 12, 13 are advantageously formed by partitioning, by compression in its middle, an initially single chamber defined by the joint membrane 30 forming its inner wall on the one hand and by the flexible band 16 forming its dorsal wall on the other hand.

More specifically, as shown in FIG. 4, the joint membrane 30, considered in its cross section, may present in fine a profile consisting of two arched domes 31, 32 protruding towards the interior of the ring 1 and standing out from the inner side 161 of the flexible band 16, said domes being separated by an intermediate section 33 close to said inner side 161 of the flexible band, and preferably bonded in an impervious manner to the latter.

In other terms, tightening chambers 12, 13 may advantageously form, at least when they are filled with fluid, two annular coils protruding towards the inside of the ring, said coils being piled up and separated from each other by a transition area forming a recess that may form the clearance area.

To complete the fixation, the joint membrane 30 may also extend by one or several flaps 34, 35 retaining it against the dorsal side of the flexible band 16.

According to a preferential variant of the invention, the portion of the joint membrane 30 corresponding to the clearance area 20 will be joined side by side against the inner side 161 of the flexible band roughly over the entire perimeter of loop 2, that is, roughly over the entire length of said flexible band 16, except for the portion located opposite the joint admission collector 17, in which a slight recess between the joint membrane 30 and the flexible band 16 advantageously lets the filling fluid circulate between the tightening chambers 12, 13 via said collector.

It is remarkable that the use of a joint membrane 30 associated with a same flexible band 16 can be used to make a simple and light structure while guaranteeing the optimum impermeability of the tightening chambers 12, 13.

According to another variant of the invention (not represented), the first and second tightening chambers 12, 13 are made separately, then each are in turn placed on the flexible band 16, preferably by bonding. Each chamber may, for example, be formed by rolling an elastomer membrane so as to create an individual tubular pouch.

Moreover, as shown in the figures, the first and second tightening chambers 12, 13 approximately extend parallel to each other, in a roughly normal manner to the rectilinear extension axis (XX').

In addition, the shape and dimensions of said tightening chambers 12, 13 preferably present are roughly identical, so that the ring in the invention has a sagittal symmetry with respect to a plane roughly normal to the axis of extension (XX') and located halfway between the two tightening chambers 12, 13.

Of course, it is perfectly possible to consider, within the invention, to have more than two stepped tightening chambers, so as to globally form a ring corresponding to a stack of several elementary rings, preferably separated two by two by clearance areas and in a particularly preferential manner all connected by the same admission circuit in joint filling fluid.

Of course, the specialist will also be able to determine the suitable dimensions of ring 1, tightening chambers 12, 13 and the clearance area 20 according to the desired application.

In particular, it is also possible to foresee tightening chambers of different dimensions, and in particular distinct re-entering volumes and/or diameters, so that the ring 1 presents a more pronounced constriction at certain levels than at others.

In addition, according to a variant of the invention that may constitute an invention as such, the ring 1 may comprise a plurality of ring tightening chambers, and in particular three chambers, axially stacked and roughly side by side to each other away from their respective contract areas with the stomach wall, so as to form a sort of adaptable « caterpillar » or sleeve consisting of elementary rings jointed to each other, thereby letting the gastric ring adopt the shape of the stomach in all circumstances.

Purely as an indication, a gastric ring according to the invention may present the following dimensions
  Thickness measured between the two lateral edges of the ring according to the extension medium axis (XX') approximately between 10 mm and 30 mm.
  Nominal tightening diameter (that is, the diameter of the inset portions of the tightening chambers when inflated, measured crosswise at the extension medium axis (XX')) approximately between 8 mm and 30 mm.
  Clearance diameter (measured crosswise to the axis of extension (XX') at the bottom of the recess (21) approximately between 30 mm and 35 mm.

Thickness of each chamber (width of the base of the cross section of the cavity, measured in parallel to the axis of extension (XX') approximately between 4 mm and 12 mm.

Clearance height (width of the recess 21 measured in parallel to the axis of extension (XX') and corresponding to the separation between the first and the second chamber) approximately between 0 mm (chambers side by side at their base) and 10 mm.

Moreover, the invention also relates to a method to manufacture an implantable surgical ring 1 as described above, and more specifically an implantable surgical ring designed to be closed on itself to form a closed loop having an extension medium axis (XX') for tightening a biological organ 3 forming a pouch or duct in order to modify the cross section of flow into said organ.

According to the invention, said method comprises a step (a) of preparation during which at least one ring tightening chamber 12 and a second ring tightening chamber 13 are created, each designed to contain a filling fluid.

Such a preparation step may in particular include a shaping sub-step, in particular by injection of moulding of one or several elastomer membranes designed to delimit said tightening chambers.

In addition, the method in the invention comprises a step (b) involving stepping during which said first and second tightening membranes are mechanically connected to each other by being stepped along the extension medium axis (XX') of the loop so that the ring 1 is able to tighten the organ 3 at the level of at least two axially separated contact areas 14A, 14B.

More specifically, said step (b) involving stepping may comprise an assembly sub-step (b1) during which the first and the second tightening chambers 12, 13 are attached to the inner side of a single flexible band 16, as well as a delimitation sub-step (b2) during which a material-free clearance area 20 is created between said first and second tightening chambers 12, 13.

In a particularly preferential manner, the delimitation sub-step (b2) comprises a junction phase to create a recess, during which is placed, opposite the inner side 161 of the flexible band 16, a membrane 30 common to the first and second tightening chambers 12, 13, then the portion of said joint membrane 30 corresponding to the clearance area 20 is placed against said flexible band 16 in order to have it adhere to the latter.

In a particularly advantageous manner, this operation may be carried out flat, that is, while the flexible band 16 is unrolled, by means of a stamping or rolling method during which a stamp or a tool crushes the central part of the joint membrane 30, so as to divide the initially single and joint pouch into two distinct tightening chambers 12, 13.

Advantageously, this junction phase to create a recess is only used on a portion of the contour of loop 2, that is, the length of the flexible band 16, so as to preserve at least one area of free communication between the first and second tightening chambers 12, 13, preferably opposite the admission collector 17.

Finally, the method in the invention also comprises a fluidic arrangement step (c) during which either a free 2-way fluidic communication is provided between the first and second tightening chambers 12, 13, or said chambers are roughly isolated from each other.

More specifically, a free 2-way fluidic communication may be obtained by preserving or by creating one or several communication openings between said chambers. On the contrary, it is also possible to roughly isolate said chambers, either in an impervious manner by means of one or several possibly separate walls, or by a joint partition possibly presenting a slight porosity.

Thereby, the method of manufacture in the invention may be used to create a surgical ring providing excellent stability once implanted in an especially simple, fast and inexpensive manner.

In addition, such a ring in the invention considerably limits the traumatism of the patient and improves the long-term comfort and reliability of the treatment.

Finally, the structure of the ring according to the invention makes it light, compact and easy to use, all of which is especially appreciable both by the practitioner and by the patient.

Possibility of Industrial Application

The invention has an industrial application in the design and manufacture of implantable medical devices in particular for the treatment of obesity.

The invention claimed is:

1. An apparatus for tightening a biological organ that forms at least one of a pouch and a duct to change a cross-section of flow into said biological organ, said apparatus comprising:
    an implantable surgical ring having an open state and a closed state, wherein in said closed state, said implantable surgical ring forms a closed loop having an extension-medium axis, wherein said implantable surgical ring comprises:
        a flexible band having a length that corresponds to said loop,
        a first ring-tightening chamber attached to an inner side of said flexible band and protruding radially inward therefrom when said implantable surgical ring forms said closed loop, and
        a second ring-tightening chamber attached to an inner side of said flexible band and protruding radially inward therefrom when said implantable surgical ring forms said closed loop,
    wherein said first ring-tightening chamber is attached to said second ring-tightening chamber,
    wherein said first and second ring-tightening chambers are configured to accommodate filling fluid,
    wherein said implantable surgical ring is configured to transition into a filling-fluid inflated state in which said implantable surgical ring tightens said biological organ by filling said first and said second ring-tightening chambers with filling fluid,
    wherein said first and second ring-tightening chambers are stepped along said extension-medium axis to an extent sufficient to avoid contacting each other when said surgical ring has transitioned into said filling-fluid inflated state,
    wherein, when said implantable surgical ring is in said filling-fluid inflated state, in which said implantable surgical ring is tightening said biological organ, said first ring-tightening chamber is configured to contact said biological organ along a first contact area, and said second ring-tightening chamber is configured to contact said biological organ along a second contact area, said first contact area being axially separate from said second contact area, there being a material-free clearance area between said first contact area and said second contact area,
    wherein said implantable surgical ring is configured to enable said biological organ to move without contacting said implantable surgical ring.

2. The apparatus of claim 1, wherein said material-free clearance area extends over a perimeter of said loop.

3. The apparatus of claim 1, wherein said implantable surgical ring comprises an anti-proximity element placed between said first ring-tightening chamber and said second ring-tightening chamber, wherein said anti-proximity element is configured to maintain a predetermined minimum separation between said first ring-tightening chamber and said second ring-tightening chamber.

4. The apparatus of claim 3, wherein said anti-proximity element is formed by a reinforced portion of said flexible band.

5. The apparatus of claim 1, wherein said material-free clearance area comprises a recess on said inner side of said flexible band, wherein a bottom of said recess is set back from said first and second ring-tightening chambers.

6. The apparatus of claim 1, wherein said implantable surgical ring comprises means for causing axial clearance of said first and second ring-tightening chambers to be within predefined limits.

7. The apparatus of claim 1, wherein said first and second ring-tightening chambers are parallel to each other.

8. The apparatus of claim 1, further comprising a joint membrane configured to be in contact with said biological organ to be tightened, wherein said first and second ring-tightening chambers are delimited by said joint membrane.

9. The apparatus of claim 8, wherein at least part of said joint membrane is side-by-side against said inner side of said flexible band to form said material-free clearance area.

10. The apparatus of claim 1, wherein said first and second ring-tightening chambers are in free two-way fluid communication.

11. The apparatus of claim 1, wherein said first and second ring-tightening chambers are in fluid isolation from each other.

12. The apparatus of claim 1, further comprising a catheter for transferring external fluid into said implantable surgical ring, wherein said implantable surgical ring includes a joint admission collector that receives said catheter and provides fluid communication between said first and second tightening chambers.

13. The apparatus of claim 12, wherein said joint admission collector is integrated in said implantable surgical ring and opens symmetrically on each of said first and second tightening chambers.

14. The apparatus of claim 1, wherein said implantable surgical ring forms a gastroplasty ring.

15. The apparatus of claim 1, wherein said material-free clearance area has a volume that is independent of an extent to which said first and second ring-tightening chambers are filled with filling fluid.

16. A method for manufacturing an implantable surgical having an open state and a closed state, wherein in said closed state, said implantable surgical ring forms a closed loop having an extension-medium axis, wherein said implantable surgical ring comprises:
 a flexible band having a length that corresponds to said loop,
 a first ring-tightening chamber attached to an inner side of said flexible band and protruding radially inward therefrom when said implantable surgical ring forms said closed loop, and
 a second ring-tightening chamber attached to an inner side of said flexible band and protruding radially inward therefrom when said implantable surgical ring forms said closed loop,
 wherein said first ring-tightening chamber is attached to said second ring-tightening chamber,
 wherein said first and second ring-tightening chambers are configured to accommodate a filling fluid that causes said implantable surgical ring to transition into a filling-fluid inflated state in which said implantable surgical ring tightens a biological organ,
 wherein said first and second ring-tightening chambers are stepped along said extension-medium axis to an extent sufficient to avoid contacting each other when said surgical ring has transitioned into said filling-fluid inflated state,
 wherein, when said implantable surgical ring is in said filling-fluid inflated state, in which said implantable surgical ring is tightening said biological organ, said first ring-tightening chamber contacts said biological organ along a first contact area, and said second ring-tightening chamber contacts said biological organ along a second contact area, said first contact area being axially separate from said second contact area, there being a material-free clearance area between said first contact area and said second contact area to enable said biological organ to move without contacting said implantable surgical ring,
said method comprising:
creating said first ring-tightening chamber configured to contain said filling fluid,
connecting said first ring-tightening chamber to said inner side of said flexible band having a length that corresponds to said loop,
creating said second ring-tightening chamber configured to contain said filling fluid,
connecting said second ring-tightening chamber to said inner side of said flexible band,
mechanically connecting said first ring-tightening chamber to said second ring-tightening chamber such that said first ring-tightening chamber and said second ring-tightening chamber are separated along said extension-medium axis of said loop,
wherein mechanically connecting said first ring-tightening chamber to said second ring-tightening chamber comprises ensuring an axial clearance such that, when said implantable surgical ring is in said filling-fluid inflated state, said first ring-tightening chamber contacts said biological organ at said first contact area, said second ring-tightening chamber contacts said biological organ at said second contact area that is axially separated from said first contact area, and said material-free clearance area exists between said first contact area and said second contact area such that said biological organ may move without contacting said implantable surgical ring and such that said first and second ring-tightening chambers tighten said biological organ at said first and second contact areas.

17. The method of claim 16, further comprising placing, opposite said inner side of said flexible band, a membrane common to said first and second ring-tightening chambers, and bringing a portion of a joint membrane corresponding to said clearance area against said flexible band so as to cause said joint membrane to adhere to said flexible band.

18. The method according to claim 16, wherein said material-free clearance area has a volume that is independent of an extent to which said first and second ring-tightening chambers are filled with filling fluid.

* * * * *

UNITED STATES PATENT AND TRADEMARK OFFICE
CERTIFICATE OF CORRECTION

PATENT NO.         : 8,721,522 B2
APPLICATION NO.    : 12/738101
DATED              : May 13, 2014
INVENTOR(S)        : Jean-Paul Ricol It is certified that error appears in the above-identified patent and that said Letters Patent is hereby corrected as shown below:

In the Claims

In column 13, claim 16, lines 50-54 please amend to read "A method for manufacturing an implantable surgical having an open state and a closed state, wherein in said closed state, said implantable surgical ring forms a closed loop having an extension-medium axis, wherein said implantable surgical ring comprises:"

In column 14, claim 16, lines 1-2 please amend to read "wherein said first ring-tightening chamber is attached to said second ring-tightening chamber"

Signed and Sealed this
Fifth Day of August, 2014

Michelle K. Lee
*Deputy Director of the United States Patent and Trademark Office*